US00PP24150P3

(12) United States Plant Patent
Egger

(10) Patent No.: US PP24,150 P3
(45) Date of Patent: Jan. 7, 2014

(54) ***HEUCHERA* PLANT NAMED 'CAJUN FIRE'**

(50) Latin Name: ***Heuchera* hybrid**
Varietal Denomination: Cajun Fire

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 148 days.

(21) Appl. No.: 13/385,800

(22) Filed: Mar. 6, 2012

(65) Prior Publication Data

US 2013/0239279 P1 Sep. 12, 2013

(51) Int. Cl.
*A01H 5/00* (2006.01)

(52) U.S. Cl.
USPC ..... Plt./440

(58) Field of Classification Search
USPC ..... Plt./440
See application file for complete search history.

*Primary Examiner* — June Hwu
(74) *Attorney, Agent, or Firm* — Klarquist Sparkman, LLP

(57) ABSTRACT

A new and distinct *Heuchera* plant characterized by medium, jagged edged leaves, red spring to very dark summer through winter leaf color, creamy white flowers on short dark stalks, medium, mounding habit, and excellent vigor.

1 Drawing Sheet

Botanical denomination: *Heuchera* hybrid.
Variety designation: 'Cajun Fire'.

BACKGROUND OF THE INVENTION

The present invention relates to a new and distinct cultivar of *Heuchera* and given the cultivar name of 'Cajun Fire'. *Heuchera* is in the family Saxifragaceae. *Heuchera* 'Cajun Fire' originated from a cross between *Heuchera* 1059-3, a proprietary non-commercial hybrid, as the seed parent, and *Heuchera* 1059-4, a proprietary non-commercial hybrid, as, as the pollen parent.

Compared to the seed parent and pollen parents, the new cultivar has red to very dark brown leaves rather than dark to khaki leaves and it has almost no veil on the leaf rather than an obvious veil.

Compared to *Heuchera* 'Sparkling Burgundy', U.S. Plant Pat. No. 17,208, the new cultivar has darker leaves, with the spring leaves more red rather than purple in color, darker veins, and whiter flowers.

This new *Heuchera* is uniquely distinguished by:

1. medium, jagged edged leaves,
2. red spring to very dark summer through winter leaf color,
3. creamy white flowers on short dark stalks,
4. medium, mounding habit,
5. excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows a 9-month-old plant of *Heuchera* 'Cajun Fire' in bloom growing in the trial field in full sun in early June in Canby, Oreg.

FIG. 2 shows a 2-year-old plant in late July in the garden in Canby, Oreg.

DETAILED PLANT DESCRIPTION

The following is a detailed description of the new *Heuchera* cultivar based on observations taken in early June of one-and-a-half-year-old specimens growing in two gallon containers, grown outside, in May in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form.*—Basal rosette, herbaceous perennial.
*Hardiness.*—USDA Zone 4 to 9.
*Size.*—17 cm tall from top of the foliage to the ground and 32 cm wide.
*Habit.*—Mounding.
*Vigor.*—Excellent.

Leaf:

*Type.*—Simple.
*Arrangement.*—Rosette.
*Shape.*—Ovate to orbicular.
*Lobing/division.*—5 to 7 shallow lobes, shallow secondary lobes.
*Venation.*—Palmate.
*Margins.*—Broadly crenate.
*Apex.*—Mucronulate.
*Base.*—Cordate, lobes overlapping at the base.
*Blade size.*—Grows to 8 cm long and 7.5 cm wide.
*Texture.*—Leathery.
*Surface texture.*—Glandular pubescent on both sides.
*Petiole description.*—Grows to 14.5 cm long and 2.5 mm wide, glandular hairs, Greyed Purple 187C.
*Leaf color.*—New spring leaves topside, Greyed Purple 183C, bottom side Red Purple 59B; mature spring leaves topside Greyed Purple 183A with lighter areas on the raised surfaces Greyed Purple 184C, bottom side Red Purple 59B; summer through winter leaves topside Greyed Purple 187B, bottom side Red Purple 59B.

Inflorescence:

*Size.*—Grows to 8.5 cm wide and 21 cm long.

*Type.*—Thyrse.

*Number of flowers per thyrse.*—About 55.

*Number of thyrse.*—About 10 in the first spring flush.

*Peduncle.*—Grows to 21 cm long and 3 mm wide at base, Greyed Purple 187A, glandular hairs.

*Pedicel.*—1.5 mm to 4 mm, with glandular hairs, Greyed Purple 187B.

*Bloom period.*—May through June in Canby, Oreg.

Flower bud:

*Size.*—3 mm wide and 4 mm long.

*Description.*—Glandular puberulent, ovoid, down facing.

*Color.*—White 155A.

Flower:

*Type.*—Perfect.

*Shape.*—Campanulate.

*Size.*—6 mm long and 4 mm wide.

*Corolla description.*—5 petals, 3 mm long and 1 mm wide, spatulate, reflexed, margins entire, tip acute, glandular hairs on bottom and glabrous on top, White NN155A.

*Calyx description.*—Campanulate, 6 mm long and 3 mm wide, with 5 lobes divided ½ way to the base, each 2 mm wide and 3 mm long, glandular hairs inside and out, tip obtuse, margin entire; color both sides White 155B with tints of Greyed Purple 186A on back side.

*Stamen description.*—5 in number, filaments 2 mm long, White NN155B, anthers 0.4 mm, Greyed Orange 168B, pollen none.

*Pistil description.*—1, 2-beaked, 5 mm long and 2 mm wide; ovary 2 mm long and 2 mm wide, White 155A; style 3 mm long, White 155A.

*Fragrance.*—None.

*Lastingness.*—Each thyrse blooms for about 3 weeks on the plant.

Fruit:

*Type.*—Two-beaked ovoid capsule.

*Fertility.*—Low.

*Color.*—Greyed Brown 199C.

Seed:

*Shape.*—Linear.

*Size.*—2 mm long.

*Color.*—Black 202A.

Pest and disease tolerance: Excellent disease resistance to powdery mildew, the common problem of *Heuchera*. Susceptible to *Heuchera* rust and root weevils.

I claim:

1. A new and distinct *Heuchera* plant as herein illustrated and described.

* * * * *

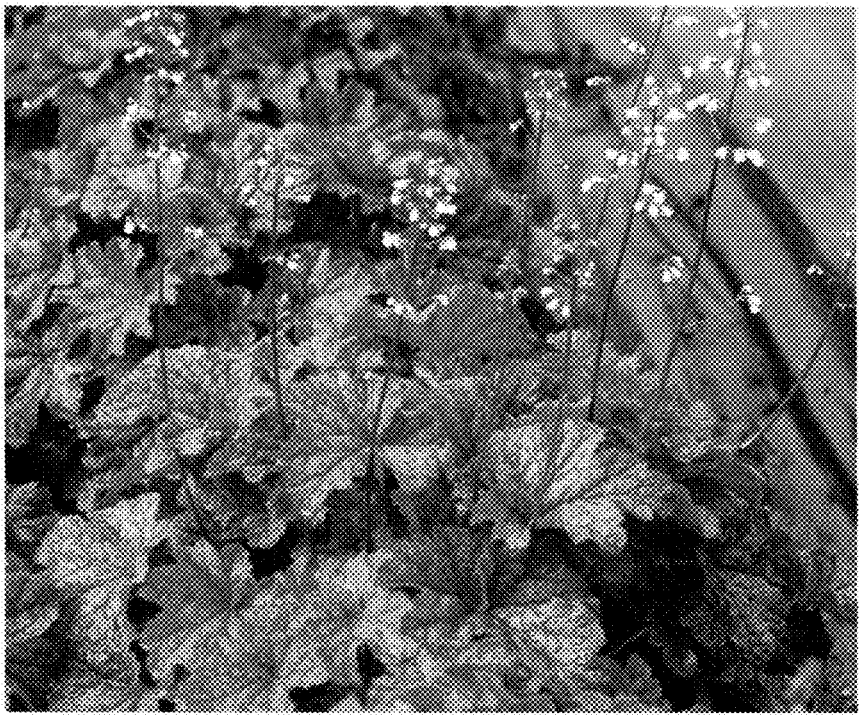
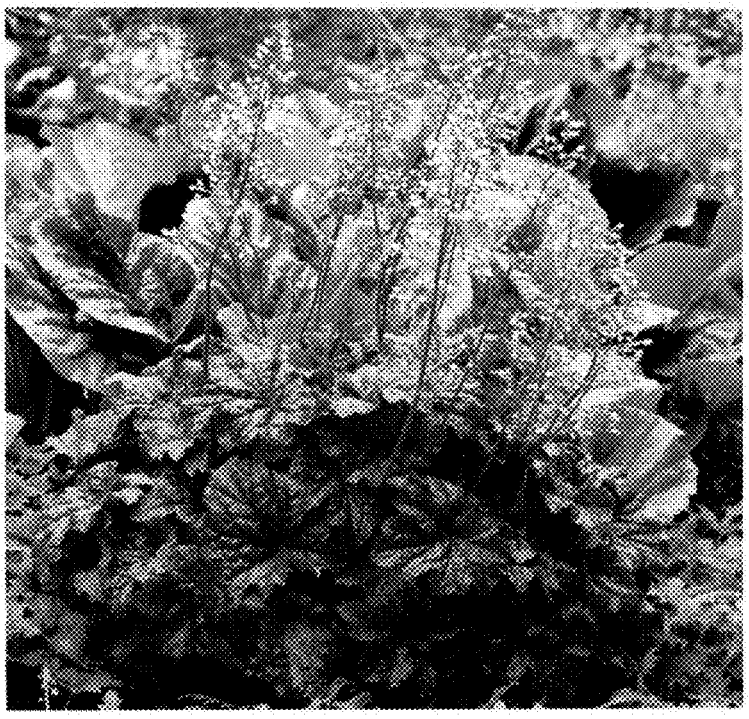
FIG. 1 above
FIG. 2 to left